US009629890B2

(12) United States Patent
Gerhardt et al.

(10) Patent No.: US 9,629,890 B2
(45) Date of Patent: Apr. 25, 2017

(54) PEPTIDES CONTAINING TRYPTOPHAN

(75) Inventors: Cindy Gerhardt, Basel (CH); Joris Kloek, Basel (CH); Rob Markus, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/877,561

(22) PCT Filed: Sep. 28, 2011

(86) PCT No.: PCT/EP2011/066801
§ 371 (c)(1),
(2), (4) Date: Jul. 1, 2013

(87) PCT Pub. No.: WO2012/045617
PCT Pub. Date: Apr. 12, 2012

(65) Prior Publication Data
US 2013/0296232 A1    Nov. 7, 2013

(30) Foreign Application Priority Data

Oct. 5, 2010    (EP) .................... 10186571

(51) Int. Cl.
*C12P 21/06*    (2006.01)
*A61K 38/01*    (2006.01)
*A61K 38/47*    (2006.01)
*A23L 33/18*    (2016.01)

(52) U.S. Cl.
CPC ............ *A61K 38/018* (2013.01); *A23L 33/18* (2016.08); *A61K 38/47* (2013.01); *C12P 21/06* (2013.01); *A23V 2002/00* (2013.01)

(58) Field of Classification Search
None
See application file for complete search history.

(56) References Cited

U.S. PATENT DOCUMENTS

| 2004/0058866 | A1 | 3/2004 | Mallee et al. | |
| 2004/0254122 | A1 | 12/2004 | Hayes et al. | |
| 2005/0089546 | A1 | 4/2005 | Wurtman et al. | |
| 2006/0257497 | A1 | 11/2006 | Bartels-Arntz et al. | |
| 2009/0105120 | A1 | 4/2009 | Mallee et al. | |
| 2009/0270337 | A1 | 10/2009 | Van Beckhoven et al. | |
| 2010/0087359 | A1 | 4/2010 | Bartels-Arntz et al. | |
| 2011/0086803 | A1* | 4/2011 | De Roos et al. | 514/17.5 |
| 2011/0110919 | A1 | 5/2011 | Gerhardt et al. | |
| 2013/0296232 | A1* | 11/2013 | Gerhardt et al. | 514/4.9 |

FOREIGN PATENT DOCUMENTS

| CN | 101535494 | * | 9/2009 | ............. C12P 21/06 |
| CN | 101535494 A | | 9/2009 | |
| WO | WO 02/46210 | | 6/2002 | |
| WO | WO 2004/069265 | | 8/2004 | |
| WO | WO 2008/052995 | | 5/2008 | |
| WO | WO 2008052995 | * | 5/2008 | ............. C12P 21/06 |
| WO | WO 2009/133055 | | 11/2009 | |

OTHER PUBLICATIONS

Markus et al. I, "The Bovine Protein A-Lactalbumin Increases the Palsma Ratio of Tryptophan to the Other Large Neutral Amino Acids and in Vulnerable Subjects Raises Brain Serotonin Activity, Reduces Cortisol Concentration and Improves Mood Under Stress 1-3", The Am. J. of Clin Nutr, Am. Society for Nutrition, vol. 71, Jan. 1, 2000, pp. 1536-1544.*
Markus et al. II, "Whey Protein Rich in Alpha-Lactalbumin Increases the Ratio of Plasma Tryptophan to the Sum of the Other Large Neutral Amino Acids and Improves Cognitive Performance in Stress-Vulnerable Subjects", The American Journal of Clinical Nutrition, vol. 75, No. 6, Jun. 1, 2002, whole document.*
Markus et al. III, "Effect of Different Tryptophan Sources on Amino Acids Availability to the Brain and Mood in Heathy Volunteers", British Journal of Nutrition, vo. 201, No. 1, Jan. 1, 2008, pp. 107-114.*
Verschoor et al., "Effects of an Acute Alpha-Lactalbumin Manipulation on Mood and Food Hedonics in High-and Low-Trait Anxiety Individuals" British Journal of Nutrition, vol. 104, No. 4, Aug. 1, 2010 pp. 595-602.*
International Search Report for PCT/EP2011/066801 mailed Feb. 24, 2012.
E.Verschoor et al., "Effects of an Acute Alpha-Lactalbumin Manipulation on Mood and Food Hedonics in High-and Low-Trait Anxiety Individuals" British Journal of Nutrition, vol. 104, No. 4, Aug. 1, 2010 pp. 595-602.
C. Markus et al., "The Bovine Protein A-Lactalbumin Increases the Palsma Ratio of Tryptophan to the Other Large Neutral Amino Acids and in Vulnerable Subjects Raises Brain Serotonin Activity, Reduces Cortisol Concentration and Improves Mood Under Stress 1-3", The American Journal of Clinical Nutrition, American Society for Nutrition, vol. 71, Jan. 1, 2000, pp. 1536-1544.
C. Markus et al., "Whey Protein Rich in Alpha-Lactalbumin Increases the Ratio of Plasma Tryptophan to the Sum of the Other Large Neutral Amino Acids and Improves Cognitive Performance in Stress-Vulnerable Subjects", The American Journal of Clinical Nutrition, vol. 75, No. 6, Jun. 1, 2002, whole document.
C. Markus et al., "Effect of Different Tryptophan Sources on Amino Acids Availability to the Brain and Mood in Healthy Volunteers", British Journal of Nutrition, vol. 201, No. 1, Jan. 1, 2008, pp. 107-114.
M. Veldhorst et al., "A Breakfast with Alpha-Lactalbumin, Gelatin, or Gelatin + TRP Lowers Energy Intake at Lunch Compared with a Breakfast with Casein, Soy, Whey, or Whey-GMP", Clinical Nutrition, vol. 28, No. 2, Apr. 1, 2009, pp. 0261-5614.
Machine translation of CN 101535494 A.

(Continued)

*Primary Examiner* — Maury Audet
(74) *Attorney, Agent, or Firm* — Nixon & Vanderhye P.C.

(57) ABSTRACT

The present invention relates to a composition comprising a tryptophan-containing peptide and having a Trp/LNAA ratio of more than 0.1 for decreasing eating or appetite during or after stress.

10 Claims, 1 Drawing Sheet

(56) References Cited

OTHER PUBLICATIONS

Office Action issued in Chinese Patent Application No. 2011-80048202.8 dated Feb. 27, 2014.

* cited by examiner

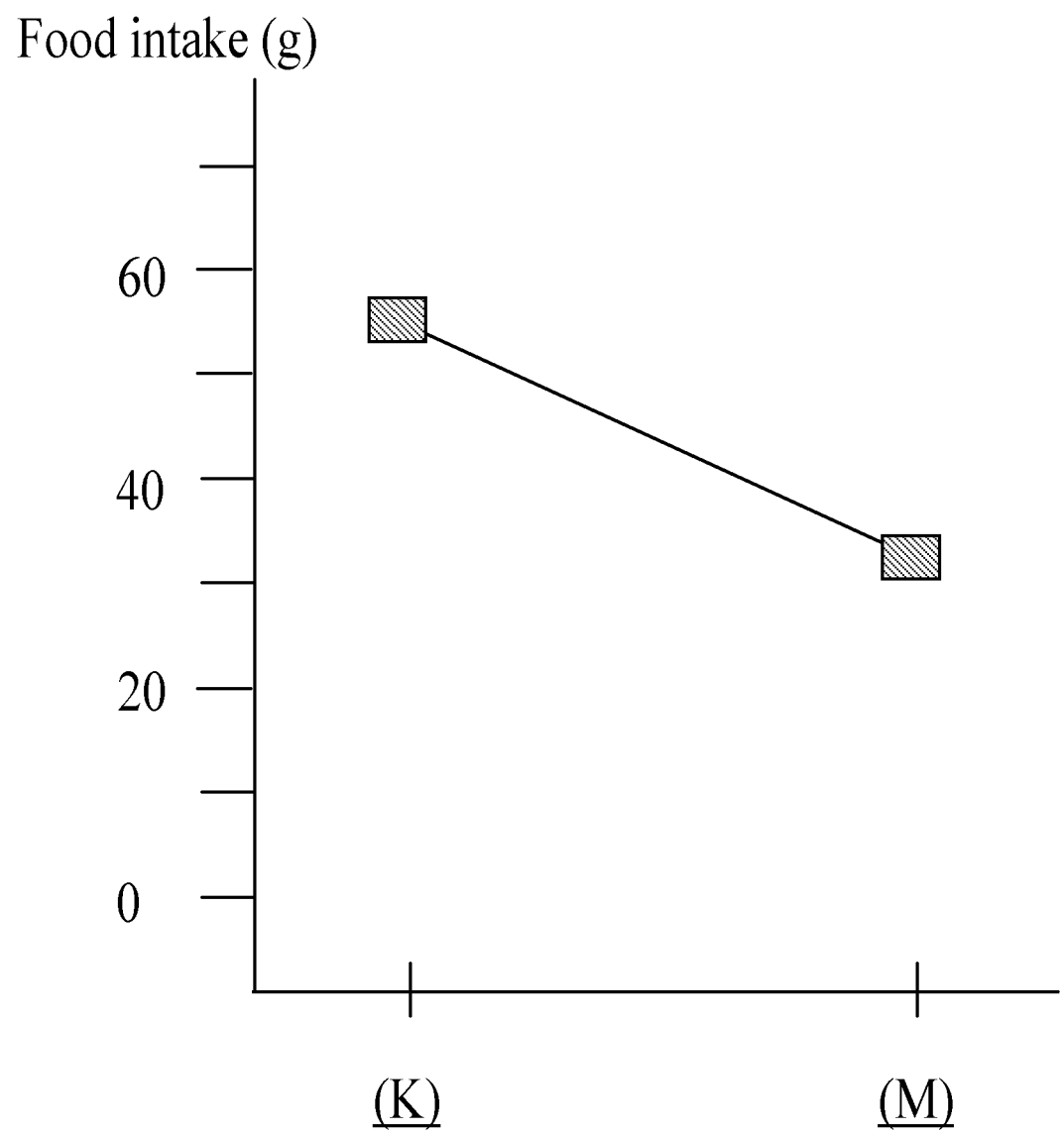

PEPTIDES CONTAINING TRYPTOPHAN

This application is the U.S. national phase of International Application No.PCT/EP2011/066801 filed 28 Sep. 2011 which designated the U.S. and claims priority to EP 10186571.5 filed 5 Oct. 2010, the entire contents of each of which are hereby incorporated by reference.

FIELD OF THE INVENTION

The present invention relates to reduced snacking during and after stress exposure.

BACKGROUND OF THE INVENTION

Stress often affects food preference and intake. Although stress can cause hypophagia, abundant studies consistently reveal that mild to moderate acute stress increases sweet high-fat food preference and intake stress-induced emotional eating may be attributed to diminished serotonergic (5-HTergic) neurotransmission or function.

Serotonine levels in the brain have been linked with mood, alertness, vigilance, sleep onset and quality, anxiolytic effects, depression, affective reaction control, appetite and sexual behavior. Many publications exist in which changes in brain serotonin levels are correlated with the availability of the natural amino acid L-tryptophan (Trp or W). Because of this correlation, methods to increase plasma tryptophan levels have received a lot of attention. Tryptophan quantities of around 1 gram/day per individual have been reported to yield clinically significant effects (Markus et al., Am. J Clin. Nutr 2005;81, 1026-1033). One method to increase plasma tryptophan levels involves the consumption of protein preparations enriched in the whey protein alpha-lactalbumin. Alpha-lactalbumin preparations are readily available and have a relatively high tryptophan concentration. However, approaches in which the alpha-lactalbumine is provided as such, see for example DE 4130284 and JP 2279700, do not take into account that the main determinant of brain tryptophan and serotonin levels is not plasma tryptophan concentration alone, but the socalled Trp/LNAA ratio (Fernstrom and Wurtman. Science 1971, 173, 149-152). This Trp/LNAA ratio represents the molar ratio of tryptophan relative to the levels of Large Neutral Amino Acids (LNAA:, i.e. the sum of tyrosine, phenylalanine, leucine, isoleucine and valine) in plasma. These LNAA compete with tryptophan for uptake into the brain, presumably because the same transport mechanism across the blood-brain barrier is used. Therefore, the most effective way of increasing brain tryptophan concentrations is to supply preparations with a high Trp/LNAA ratio. A number of publications a.o. WO 02/46210, refer to the preparation of peptide fractions from alpha-lactalbumin having improved Trp/LNAA ratio's.

Obviously the use of free tryptophan, i.e. the free amino acid, would provide the simplest and cheapest approach to provide preparations with a high Trp/LNAA ratio. However, in many countries legislation exists that tightly regulates the supply of free tryptophan. The maximal allowable free tryptophan levels in its various application forms vary per country. To supply additional dietary tryptophan in a more natural way, more recent approaches aim at providing tryptophan rich proteins. As mentioned, alpha-lactalbumin as well as its hydrolysates have gained popularity as a safe option to enhance plasma tryptophan levels.

WO2008/052995 and WO02/46210 disclose a process to produce a composition comprising a tryptophan-containing peptide and having a Trp/LNAA ratio of more than 0.15 which comprises hydrolyzing lysozyme, preferably hen eggs lysozyme, to prepare a hydrolysate having a DH of between 5 and 45.

SUMMARY OF THE INVENTION

This invention relates to tryptophan-containing peptide or tryptophan-containing hydrolysate for oral consumption. Surprisingly, it was found that oral consumption of tryptophan-containing peptide or tryptophan-containing hydrolysate leads to a decreased eating or appetite evidenced by a reduced intake of food for several hours. So according to an embodiment of the invention tryptophan-containing peptide or tryptophan-containing hydrolysate is used for oral intake preferably for reducing eating or appetite.

According to one aspect of the invention tryptophan-containing peptide or tryptophan-containing hydrolysate is used for the manufacture of a nutraceutical or food for oral intake preferably for reducing eating or appetite. Thus tryptophan-containing peptide or tryptophan-containing hydrolysate is used for reducing eating or appetite. According to another aspect of the invention a method is disclosed for reducing eating or appetite which comprises the oral administering of tryptophan-containing peptide or tryptophan-containing hydrolysate to a subject in need of such treatment.

Especially the present invention has its effect in situations of stress, including acute and chronic (life) stress.

The present invention relates to a composition comprising a tryptophan-containing peptide or tryptophan-containing hydrolysate and having a Trp/LNAA ratio of more than 0.1 for decreasing eating or appetite during or after stress. The present invention also relates to a treatment to obtain decreased eating or appetite during or after stress, by oral intake of a composition comprising a tryptophan-containing peptide or tryptophan-containing hydrolysate and having a Trp/LNAA ratio of more than 0.1.

Furthermore the present invention relates to tryptophan-containing peptide or tryptophan-containing hydrolysate or a composition comprising tryptophan-containing peptide or tryptophan-containing hydrolysate for reducing eating or appetite by oral intake. This composition preferably is a food or a beverage, a dietary supplement, a nutraceutical or a feed or pet food, including cereal bars, bakery items such as cakes and cookies, liquid foods such as soups or soup powders, beverages including non-alcoholic and alcoholic drinks as well as liquid preparations to be added to drinking water and liquid food and clinical foods.

DETAILED DESCRIPTION OF THE INVENTION

Stress is thought to influence human eating behavior in a negative way. Stress may alter food intake which may result in snacking or overeating. At least two ways of stress seem to play an important role. Chronic (life) stress as well as acute stress may be associated with a greater preference for sweet and fat. The result is often weight gain and may finally lead to the development of obesity.

The present invention provides a composition comprising tryptophan present in peptide form which is very suitable for giving an effective increase of the Trp/LNAA ratio in plasma. We noted that di- and tripeptides comprising tryptophan advantageously contribute to this increase. In one embodiment of the present invention, lysozyme, preferably hen egg lysozyme is enzymatically (pre-)hydrolysed in an industrial process i.e. (hen egg) lysozyme is preferably provided in the form of a hydrolysate. Offered in the form of a hydrolysate, the gastro-intestinal absorbtion of tryptophan-containing peptides is greatly facilitated. The hydrolysate of the invention is characterized by a molecular Trp/LNAA ratio of higher than 0.1, preferably higher than 0.15. The hydrolysate of the invention preferably has a DH (Degree of Hydrolysis) of between 5 and 45, more preferably between 10 and 40.

Therefore the present invention provides the use of the composition of the invention, for example the water-soluble peptides comprising tryptophan, for the use of obtaining an increased Trp to Large Neutral Amino Acid Ratio (Trp/LNAA) ratio in plasma within 90 minutes, preferably 60 minutes, most preferably 30 minutes after uptake of the peptides or for the preparation of a neutraceutical composition for obtaining an increased Trp/LNAA ratio in plasma within 90 minutes, preferably 60 minutes, most preferably 30 minutes after uptake of the peptides. Preferably the consumption of protein or protein-containing food is at the same time or almost the same time as the tryptophan-containing peptides. Increased Trp/LNAA ratio means an increase of this ratio compared to the situation prior to the consumption or uptake of the composition of the invention.

A "protein" or "polypeptide" is defined herein as a chain comprising more than 30 amino acid residues.

A "peptide" or "oligopeptide" is defined herein as a chain of at least two amino acids that are linked through peptide bonds. The terms "peptide" and "oligopeptide" are considered synonymous (as is commonly recognized) and each term can be used interchangeably as the context requires.

A "water-soluble" peptide is a peptide which is soluble in water at a pH of 5.0.

All (oligo)peptide and polypeptide formulas or sequences herein are written from left to right in the direction from amino-terminus to carboxy-terminus, in accordance with common practice. The one-letter code of amino acids used herein is commonly known in the art and can be found in Sambrook, et al. (Molecular Cloning: A Laboratory Manual, $2^{nd}$ ed. Cold Spring Harbor Laboratory, Cold Spring Harbor Laboratory Press, Cold Spring Harbor, N.Y., 1989).

By protein hydrolysate, hydrolysate or hydrolysed protein is meant the product that is formed by enzymatic hydrolysis of a protein, an enriched hydrolysate being a fraction of the protein hydrolysate for example enriched in selected peptides or wherein peptides or polypeptides have been removed from the hydrolysate. So an enriched hydrolysate is preferably a mixture of peptides (or a peptide mixture). The peptide mixture of the invention is therefore a mixture of at least two, preferably at least three, more preferably at least four tryptophan containing peptides. More preferably the mixture comprises a peptide population of which more than 50%, preferably even more than 60%, and most preferably more than 75% of the peptides present have a molecular weight below 500 Da. A tryphophan-containing peptide means a peptide which comprises at least one L-tryphophan amino acid residue. WO2008/052995 and WO02/46210 disclose protein hydrolysates and compositions which comprise peptide-bound tryptophan which may be used in the present invention.

The Trp/LNAA ratio represents the molar ratio of tryptophan relative to the levels of other Large Neutral Amino Acids (LNAA:, i.e. the sum of tyrosine, phenylalanine, leucine, isoleucine and valine). Except for the plasma Trp/LNAA ratio, the Trp/LNAA ratio relates only to peptide-bound amino acids. Thus free tryptophan, tyrosine, phenyl-alanine, leucine, isoleucine and valine are not taken into account in the Trp/LNAA ratio.

By tryptophan-rich composition is meant herein a composition comprising a tryptophan-containing peptide or tryptophan-containing hydrolysate and having a Trp/LNAA ratio of more than 0.1.

By tryptophan-rich hydrolysate is meant herein a hydrolysate comprising a tryptophan-containing peptide and having a Trp/LNAA ratio of more than 0.1.

Peptide-bound amino acids are amino acids which are part of a peptide and not free amino acids.

Appetite is defined as the desire to eat, stimulated by feelings of hunger.

Stress often affects food preference and intake. Abundant studies consistently reveal that chronic life stress, mild to moderate acute stress and/or negative mood increases sweet high-fat food preference and intake stress-induced emotional eating may be attributed to diminished serotonergic (5-HTergic) neurotransmission or function. Especially for this stress-induced eating snacking the present invention provides a way to decrease this snacking behaviour. Stress can come from many different situations and can be short-lived or long-lasting.

By chronic stress or chronic life stress is meant long-term stress. Chronic stress comes about as the result of a situation that has not been resolved or continued for many months or even years prior to being resolved.

By acute stress is meant short-lived stress. For example, when a deadline is approaching, Advantageously lysozyme, preferably hen egg lysozyme is enzymatically (pre-) hydrolysed in an industrial process i.e. (hen egg) lysozyme is preferably provided in the form of a hydrolysate or an enriched hydrolysate. Offered in the form of such an (enriched) hydrolysate, the intestinal absorbtion of tryptophan containing peptides is greatly facilitated. The (hen egg) lysozyme hydrolysate may be fractionated in order to increase the tryptophan content of a fraction of the hydrolysate. This fraction or enriched hydrolysate has preferably an increased Trp/LNAA ratio as compared to the hydrolysate before fractionation. The enrichment of the hydrolysate or enriched hydrolysate with additional free tryptophan, also forms part of the present invention.

The (enriched) protein hydrolysates according to the present invention, or peptide fraction obtained from this protein hydrolysate, can be used in any suitable form such as a food or a beverage, as Food for Special Nutritional Uses, as a dietary supplement, as a neutraceutical or even in feed or pet food. The lysozyme hydrolysate may be added at any stage during the normal process of these products. If used in food or beverages, products with a relatively low protein content are preferred in order to maintain the high Trp/LNAA ratio in blood after consumption of the products according to the invention. In addition, preferably carbohydrates are added to food or beverages containing lysozyme hydrolysate to even further improve the high Trp/LNAA ratio in blood after consumption. Suitable food products include e.g. cereal bars, bakery items such as cakes and cookies and also liquid foods such as soups or soup powders. Apart from dairy products such as milk and yogurt, other suitable beverages encompass non-alcoholic and alcoholic drinks as well as liquid preparations to be added to drinking water and liquid food. Non-alcoholic drinks are preferably mineral water, sport drinks, fruit juices, lemonades, teas, concentrated drinks such as shots, energy drinks (for example drinks containing glucuronolactone, caffeine or taurine) and carbonated beverages (for example pops, sodas and cola drinks). Examples of Foods for Special Nutritional Uses include the categories of sport foods and clinical foods. The term dietary supplement as used herein denotes a product taken by mouth that contains a compound or mixture of compounds intended to supplement the diet. The compound or mixture of compounds in these products may include: vitamins, minerals, herbs or other botanicals and amino acids. Dietary supplements can also be extracts or concentrates, and may be found in many forms such as tablets, capsules, softgels, gelcaps, liquids, or powders. The term neutraceutical as used herein denotes the usefulness in both the nutritional and pharmaceutical field of application. The neutraceutical compositions according to the present invention may be in any form that is suitable for administrating to the animal body including the human body, especially in any form that is conventional for oral administration, e.g. in solid form such as (additives/supplements for) food or feed, food or feed premix, tablets, pills, granules, dragées, capsules, and effervescent formulations such as powders and tablets, or in liquid form such as solutions, emulsions or suspensions as e.g. beverages, pastes and oily suspensions. Controled (delayed) release formulations incorporating the hydrolysates according to the invention also form part of the invention. Furthermore, a multi-vitamin and mineral supplement may be added to the neutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns. Because the invention relates to decreasing appetite and eating, which may affect weight gain, thencomposition of the invention preferably comprises low amounts of carbohydrates or fats to keep the composition low in calories. So the final product in which the invention is used is often a "light" product.

LEGENDS TO THE FIGURE

FIG. 1 The total food intake during interview preparation following tryptophan-rich hydrolyzed (M) and placebo protein (K) intake.

MATERIALS AND METHODS

Materials

Subtilisin under the commercial name of "Protex 6L" was obtained from Genencor (Leiden, The Netherlands).

Lysozyme was obtained as Delvozyme L (22% dry matter) from DSM Food Specialities (Delft, The Netherlands).

Amino Acid Analysis

Amino acid analyses were carried out according to the PicoTag method as specified in the operators manual of the Amino Acid Analysis System of Waters (Milford, Mass., USA). To that end samples were dried and directly derivatised using phenylisothiocyanate. The derivatised amino acids present were quantitated using HPLC methods as described. As during the usual acid hydrolysis Trp and Cys are destroyed, special methods were used to quantitate these two amino acids. To prevent Cys degradation during hydrolysis, this amino acid is first oxidized to cysteic acid using hydrogen peroxide and then quantitated. The analysis of tryptophan is based on a slightly modified Waters procedure. In this procedure an aliquot of the peptide solution is dried under vacuum and then hydrolysed during 1 hour at 150 degrees C. under nitrogen in 4M methane sulphonic acid containing 0.2% tryptamine. The reaction product is directly quantitated using HPLC equipped with an Alltech Altima C18 column and fluorescence detection.

Degree of Hydrolysis

The Degree of Hydrolysis (DH) as obtained during incubation with the various protolytic mixtures was monitored using a rapid OPA test (Nielsen, P. M.; Petersen, D.; Dambmann, C. Improved method for determining food protein degree of hydrolysis. *Journal of Food Science* 2001, 66, 642-646).

The following Examples illustrate the invention further.

EXAMPLES

Example 1

Hydrolysing Lysozyme using Protex to Produce a Tryptophan-Rich Hydrolysate

A solution containing 10% (w/w) pure lysozyme was adjusted to pH 8.2 using NaOH and heated to 52 degrees C. Hydrolysis was started by adding 25 microliter of Protex/g of protein present. Under continuous stirring and maintaining the pH at 8.2, the hydrolysis was continued for 5.5 hours to yield an almost clear solution without a visible precipitate. After a heating step to inactivate the Protex activity, a sample was taken for DH analysis. The DH of the solution turned out to be almost 30%. The heat treated solution was ultra-filtrated over a 10 kDa filter to yield a completely clear liquid (tryptophan-rich hydrolysate or tryptophan-rich hydrolyzed protein.

Example 2

Reduction of Stress-Induced Snacking Using a Tryptophan-Rich Hydrolysate

The study was conducted according to a double-blind placebo-controlled crossover design. During two experimental sessions, each of 42 participants visited the laboratory to monitor their food intake before and after acute stress exposure and following either tryptophan-rich hydrolyzed protein (THP, see Example 1) or placebo protein (PLC) intake. The order of the dietary condition was counterbalanced over the two test days with a washout period of at least one week.

Before each test day participants were instructed to refrain from alcohol for at least 36 hours and to fast 12 hours before the sessions; only water or tea without sugar was permitted.

After arrival, volunteers consumed either the THP or PLC drink. Then, participants were enabled to rest (reading or watching TV) for 2 hours. While seated in a separated room, each participant was then instructed to prepare for an interview to an unknown University staff-member panel. During this 5 minutes preparation phase, participants had free access to pre-weighed portions of snack foods and were instructed to eat as much as they wished. After the preparation phase, each pair of participants was brought together in a larger experimental room to conduct a 15 minute stress-inducing interview. After completion of the stress-inducing interview procedure, participants had 5 minutes of free access to pre-weighed portions of snack foods.

Dietary Manipulation

During both experimental sessions, a drink was consumed containing either tryptophan-rich egg protein hydrolysate, THP (DSM Delft; The Netherlands) or placebo casein protein hydrolysate (PLC, DSM Delft; The Netherlands). Key characteristics of the product are given in Table 1.

TABLE 1

Composition of the standard protein (PLC) and tryptophan-
rich protein hydrolysate (TPH) condition.

| Source | Product (g) | Trp (mg) | TRP/LNAA (mol/mol) |
|---|---|---|---|
| PLC | 4 g/200 ml | 32 | 0.02 |
| TPH | 4 g/200 ml | 235 | 0.21 |

TABLE 2

Amino acid profile of the protein used

| Amino acid profile (g) | TPH | PLC |
|---|---|---|
| Isoleucine | 143 | 152 |
| Leucine | 231 | 300 |
| Phenylalanine | 105 | 148 |
| Tyrosine | 137 | 176 |
| Valine | 131 | 204 |
| Tryptophan | 235 | 32 |

Food Intake

To measure snacking behavior, participants were presented with a food tray before (preparation) and after stress exposure; containing pre-weighed portions of snack foods (mini candy bars, pretzels and nuts). Each time after preparation and after completion of the public speaking (interview) task, the food container was weighted to determine the total amount of food intake.

Results

Analyses revealed a main Treatment effect (P=0.037), indicating a total reduction of food intake of 21 g after the THP (34 g±27 g) compared to PLC (55 g±50 g) (see FIG. 1) which demonstrates that lysozyme hydrolysate and other tryptophan-containing hydrolysate which comprises tryptophan-containing peptide decreases snacking behaviour during stress.

The invention claimed is:

1. A method for reducing eating or deceasing appetite comprising administering to a person in need of said reducing eating or decreasing appetite, a lysozyme hydrolysate comprising Trp-containing peptides,
    wherein the lysozyme hydrolysate is characterized by having a molecular Trp/Large Neutral Amino Acid (LNAA) ratio of higher than 0.15 and a degree of hydrolysis (DH) of between 5 and 45; and
    wherein the hydrolysate is administered to the person during a time when the person is experiencing stress.

2. The method according to claim 1 wherein the stress is acute stress.

3. The method according to claim 1 wherein the lysozyme hydrolysate is in the form of a food, beverage, or dietary supplement.

4. The method according to claim 3 wherein the food is in the form of a beverage.

5. The method according to claim 3 wherein the dietary supplement is in the form of a tablet, capsule, soft gel, gelcap, liquid or powder.

6. The method of claim 1 wherein the lysozyme is hen egg lysozyme.

7. The method of claim 2 wherein the lysozyme is hen egg lysozyme.

8. The method of claim 3 wherein the lysozyme is hen egg lysozyme.

9. The method of claim 4 wherein the lysozyme is hen egg lysozyme.

10. The method of claim 5 wherein the lysozyme is hen egg lysozyme.

* * * * *